US006949345B1

(12) United States Patent
Menozzi et al.

(10) Patent No.: US 6,949,345 B1
(45) Date of Patent: Sep. 27, 2005

(54) IDENTIFICATION AND CLONING OF A MYCOBACTERIAL ANTIGEN CORRESPONDING TO A HEPARIN-BINDING HAEMAGGLUTININ

(75) Inventors: Franco Menozzi, Mons-Hyon (BE); Camille Locht, Wannehain (FR)

(73) Assignees: Institut National de la Sante et de la Recherche Medicale, Paris (FR); Institut Pasteur de Lille, Lille (FR)

( * ) Notice: Subject to any disclaimer, the term of this patent is extended or adjusted under 35 U.S.C. 154(b) by 0 days.

(21) Appl. No.: 09/192,579

(22) Filed: Nov. 17, 1998

Related U.S. Application Data

(63) Continuation of application No. PCT/FR97/00886, filed on May 20, 1997.

(30) Foreign Application Priority Data

May 17, 1996 (FR) .............................. 96 06168

(51) Int. Cl.⁷ ..................... G01N 33/53; A61K 39/02; A61K 39/04
(52) U.S. Cl. ...................... 435/7.1; 424/9.1; 424/130.1; 424/141.1; 424/150.1; 424/164.1; 424/168.1; 424/184.1; 424/185.1; 424/190.1; 424/200.1; 424/248.1; 435/4; 435/7.2; 435/7.32; 435/41; 435/42; 435/440; 435/471; 530/300; 530/350; 536/23.1; 536/23.7
(58) Field of Search ............................ 424/9.1, 130.1, 424/141.1, 150.1, 164.1, 168.1, 184.1, 185.1, 190.1, 200.1, 248.1; 435/4, 7.1, 7.2, 7.32, 41, 42, 440, 471; 530/300, 350; 536/23.1, 23.7

(56) References Cited

PUBLICATIONS

Menozzi et al, "A Heparin–Binding Hemagglutinin in mycobacteria", Abstracts of the General Meeting of the American Society for Microbiology 95(0):193 (1995)—Abstract B–159 & 95ᵗʰ General Meeting of the American Society for Microbiology, Washington, DC USA, May 21–25, 1995.

Brennan et al, "Identification of a Heparin–Binding Mycobacterial Hemagglutinin", Journal of Cellular Biochemistry Supplement 0 (19B), p. 66 (1995)—Abstract B3–104 & Keystone Symposium on Molecular Mechanisms in Tuberculosis, Tamarron, Colorado, USA, Feb. 19–25, 1995.

Isaacs, "*Borrelia burgdorferi* Bind to Epithelial Cell Proteoglycans", Journal of Clinical Investigation 93:809–819 (1994).

Menozzi et al, "Heparin–Inhibitable Lectin Activity of the Filamentous Hemagglutinin Adhesin of *Bordetella pertussis*", Infection and Immunity 62(3):769–778 (1994).

Hudson et al, "Comparison of the Fibronectin–binding Ability and Antitumor Efficacy of Various Mycobacteria", Cancer Research 50:3843–3847 (1990).

Rouse et al, "Immunological Characterization of Recombinant Antigens Isolated from a *Mycobacterium avium* λgt11 Expression Library by Using Monoclonal Antibody Probes", Infection and Immunity 59(8):2595–2600 (1991).

"*Mycobacterium tuberculosis* cosmid SCY20G9", Banque De Donnees Embl, Identificateur MTCY20G9, Accession No. Z77162, Sep. 18, 1996.

Menozzi et al, "Identification of a Heparin–binding Hemagglutinin Present in Mycobacteria", Journal of Experimental Medicine 184(3):993–1001 (1996).

*Primary Examiner*—Rodney P Swartz
(74) *Attorney, Agent, or Firm*—Nixon & Vanderhye P.C.

(57) ABSTRACT

The present invention relates to peptide sequences enabling mycobacteria to adhere to host cells (e.g., epithelial cells). More particularly, the invention relates to a mycobacterial heparin-binding haemagglutinin type antigen from *M. bovis* ECG or *M. tuberculosis*. The invention also relates to a recombinant peptide sequence enabling mycobacteria to adhere to host cells. The polypeptides can be used to prepare vaccines against mycobacterial infections and for serological diagnosis of mycobacterial infections.

3 Claims, 11 Drawing Sheets

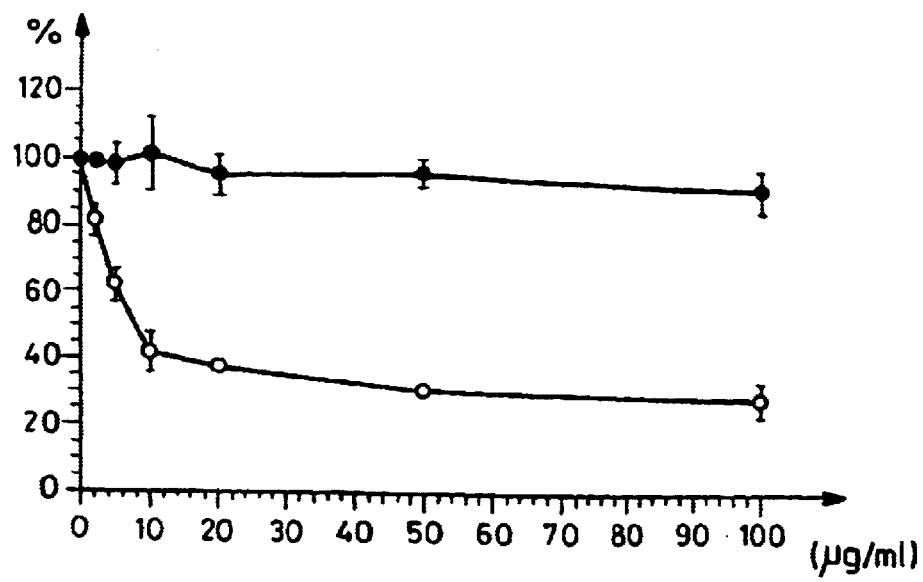
FIG_1A
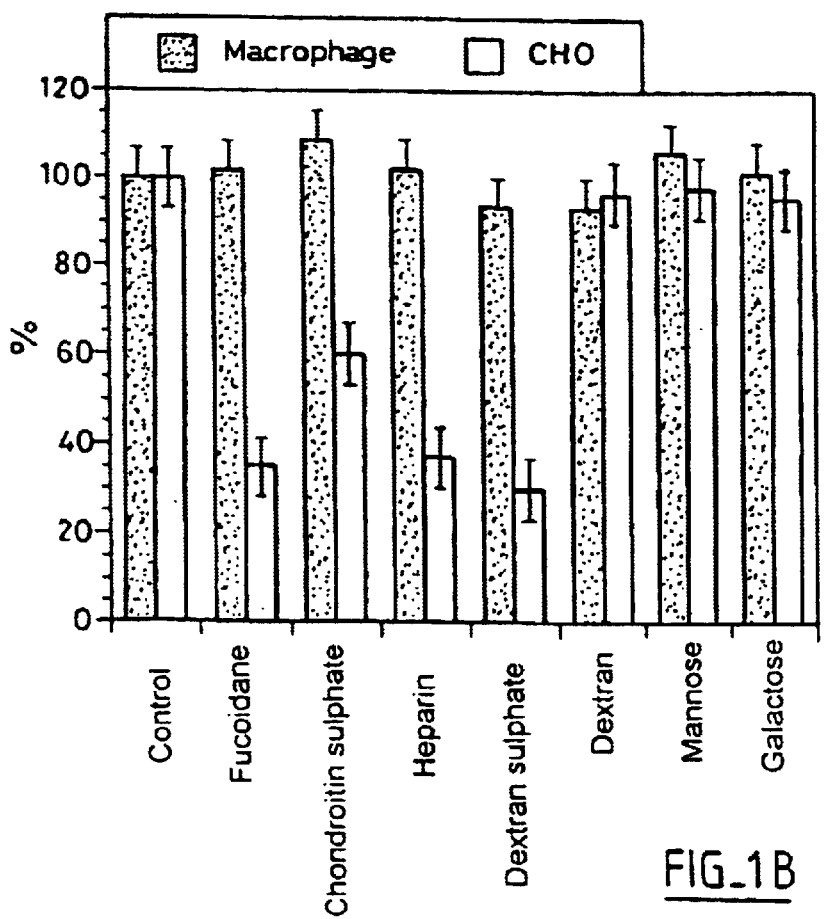
FIG_1B

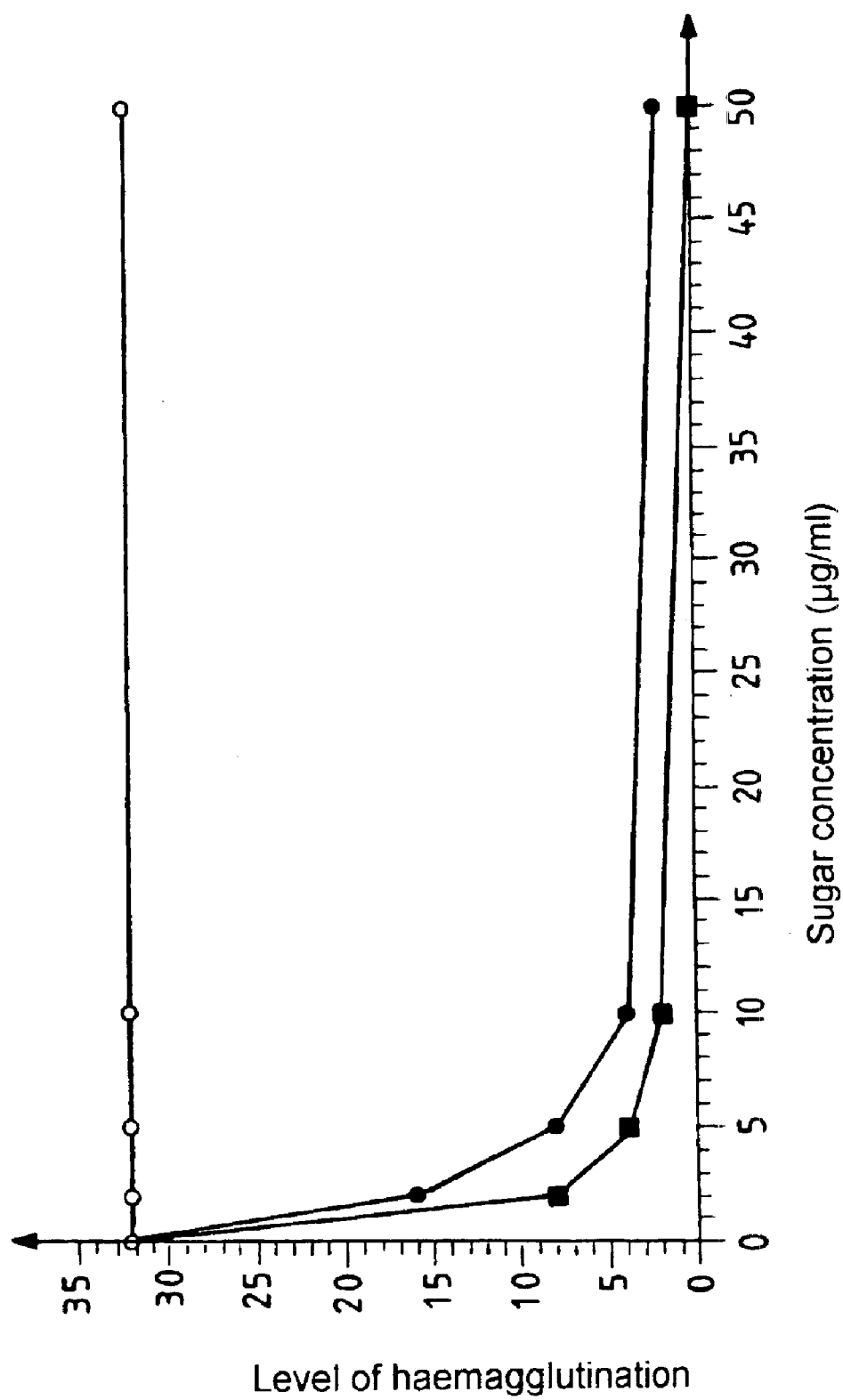
FIG_4

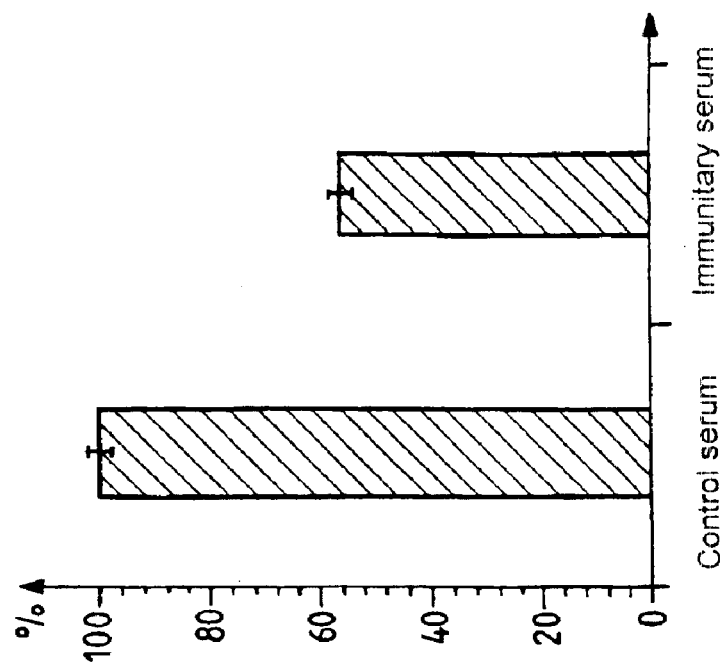
FIG._5B
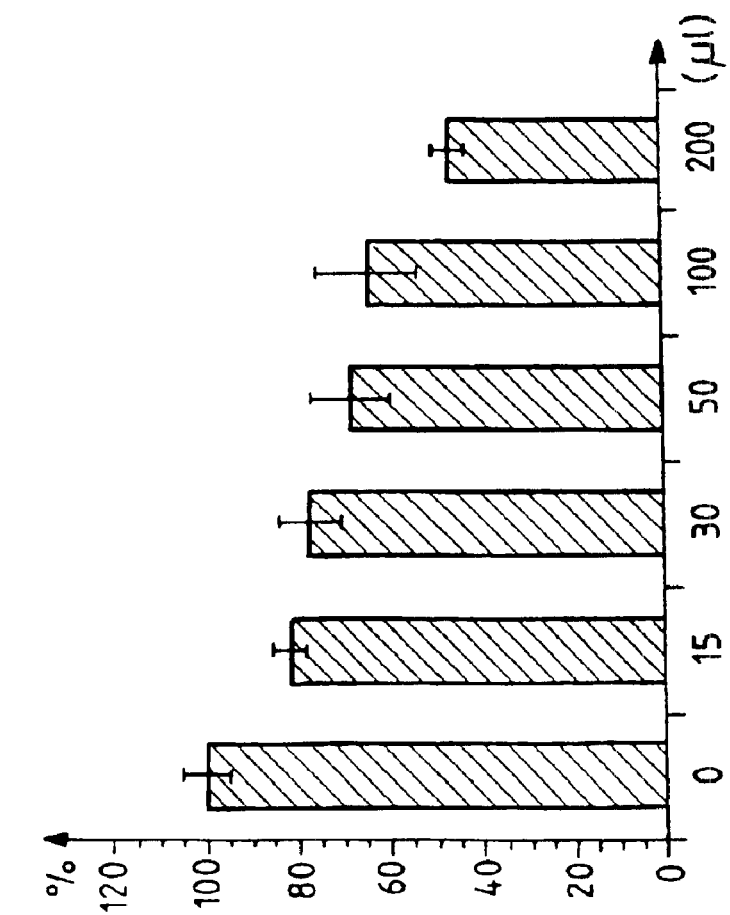
FIG._5A

Fig. 7

```
  K   A   E   G   Y   L   E   A   T   S   R   Y   N   E   L   V
aag gcc gag ggc tac ctc gag gcc act agc cgg tac aac gag ctg gtc
ttc cgg ctc ccg atg gag ctc cgg tga tcg gcc atg ttg ctc gac cag
         ────oligo 1441────

E   R   G   E   A   A   L   R   S   Q   Q   S   F   E
gag cgc ggt gag gcc gct cta cgg ctg cgc agc cag cag agc ttc gag
ctc gcg cca ctc cgg cga gat gcc gac gcg tcg gtc gtc tcg aag ctc E   V   S   A   P   A   G   Y   V   D   Q   A   V   E   L
gaa gtg tcg gcg ccc gcg ggc tac gtg gac cag gcg gtc gag ct
ctt cac agc cgc ggg cgc ccg atg cac ctg gtc cgc cag ctc ga
                                    ────oligo 1443 rev.────
```

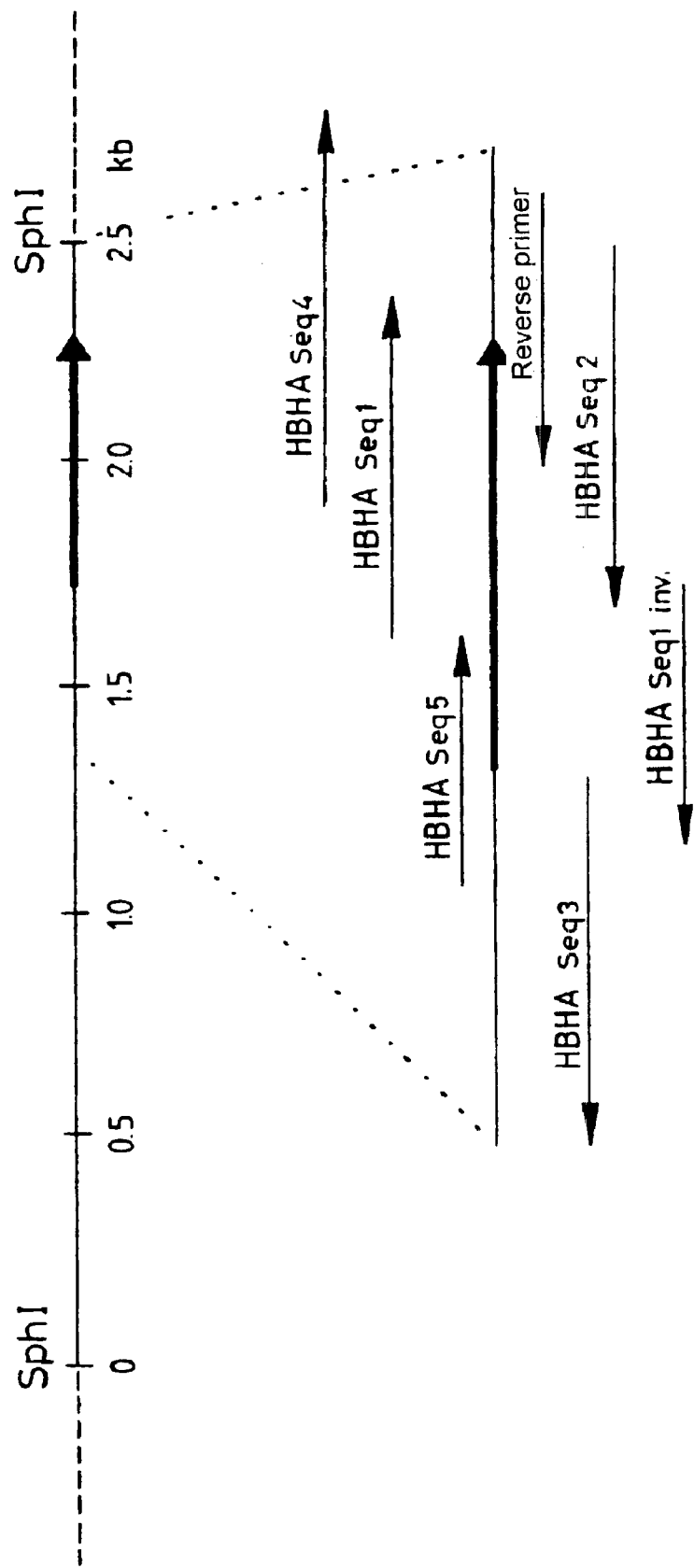
FIG_9

```
1
cgg ctg gcg ggt aat caa acc tga agg aca gtc atc tgg gtg agg tcg acc gca ggc tga 61
tcc agc cga tcg gcc ggc gct ggc caa cag cga ctc cgt cga tga cgt gca gca aag gag 121
aca tgt agt gac cgg atc agc tgg gcc tga cat cta cga act cga ccg aca acc gac ccg 181
acg atc agg agg ttt ccc cgg caa gtc gcg tgc cat gtc aat ccg cgg gtc ttg act agt 241
cct ccc tgg agg agc cga cgc ttg ccc caa cgt cca gac caa aga tgt aag aac gcc gat 301
atc aga aaa tag tta atg aaa gga ata ccc atg gct gaa aac tcg aac att gat gac atc
                                            M   A   E   N   S   N   I   D   D   I 361
aag gct ccg ttg ctt gcc gcg ctt gga gcg gcc gac ctg gcc ttg gcc act gtc aac gag
 K   A   P   L   L   A   A   L   G   A   A   D   L   A   L   A   T   V   N   E 421
ttg atc acg aac ctg cgt gag cgt gcg gag gag act cgt acg gac acc cgc agc cgg gtc
 L   I   T   N   L   R   E   R   A   E   E   T   R   T   D   T   R   S   R   V 481
gag gag agc cgt gct cgc ctg acc aag ctg cag gaa gat ctg ccc gag cag ctc acc gag
 E   E   S   R   A   R   L   T   K   L   Q   E   D   L   P   E   Q   L   T   E 541
ctg cgt gag aag ttc acc gcc gag gag ctg cgt aag gcc gcc gag ggc tac ctc gag gcc
 L   R   E   K   F   T   A   E   E   L   R   K   A   A   E   G   Y   L   E   A 601
gcg act agc cgg tac aac gag ctg gtc gag cgc ggt gag gcc gct cta gag cgg ctg cgc
 A   T   S   R   Y   N   E   L   V   E   R   G   E   A   A   L   E   R   L   R 661
agc cag cag agc ttc gag gaa gtg tcg gcg ccc gcc gaa ggc tac gtg gac cag gcg gtg
 S   Q   Q   S   F   E   E   V   S   A   P   A   E   G   Y   V   D   Q   A   V 721
gag ttg acc cag gag gcg ttg ggt acg gtc gca tcg cag acc cgc gcg gtc ggt gag cgt
 E   L   T   Q   E   A   L   G   T   V   A   S   Q   T   R   A   V   G   E   R 781
gcc gcc aag ctg gtc ggc atc gag ctg cct aag aag gct gct ccg gcc aag aag gcc gct
 A   A   K   L   V   G   I   E   L   P   K   K   A   A   P   A   K   K   A   A 841
ccg gcc aag aag gcc gct ccg gcc aag aag gcg gcg gcc aag aag gcg ccc gcg aag aag
 P   A   K   K   A   A   P   A   K   K   A   A   K   K   A   P   A   K   K 901
gcg gcg gcc aag aag gtc acc cag aag tag tcg ggc tcc gaa tca cca tcg act ccg agt
 A   A   A   K   K   V   T   Q   K   *

961
cgc cca ggg ggc gac tcg gag tcg acg tgt tgg atg caa acc gca tag tct gaa tgc gtg 1021
agc cac ctc gtg ggt acc gtc atg ctg gta ttg ctg gtc gcc gtc ttg gtg aca gcg gtg 1081
tac gcg ctt gtg cat gc
    SphI
```

Fig. 10

IDENTIFICATION AND CLONING OF A MYCOBACTERIAL ANTIGEN CORRESPONDING TO A HEPARIN-BINDING HAEMAGGLUTININ

This application is a con of PCT/Fr97/00886 May 20, 1997.

The invention relates to peptide sequences enabling mycobacteria to adhere to host cells, in particular to epithelial cells. More particularly, the invention relates to a mycobacterial heparin-binding haemagglutinin (HBHA) type antigen obtained from *Mycobacterium bovis* BCG or *Mycobacterium tuberculosis*. The invention also relates to a recombinant peptide sequence enabling mycobacteria to adhere to host cells. In particular, the invention relates to the expression product of an *Escherichia coli* strain transformed with a nucleotide sequence coding for a protein enabling mycobacteria to adhere to host cells. These polypeptides can be used in immunogenic compositions, to prepare vaccines against mycobacterial infections, and for serological diagnosis of mycobacterial infections.

The invention also relates to a nucleotide sequence coding for a peptide sequence enabling mycobacteria to adhere to host cells, and in particular a nucleotide sequence coding for a mycobacterial heparin-binding haemagglutinin (HBHA) type antigen. The invention also relates to recombinant vectors comprising said nucleotide sequence and to the use of these vectors in producing recombinant host cells which can be used in therapy, in particular in anti-cancer therapy.

Mycobacteria are among the most important pathogenic micro-organisms which cause disease in both man and in animals. Mycobacterial infections are still among the main causes of death in the world. Human tuberculosis, caused by *Mycobacterium tuberculosis*, by itself leads to approximately 3 million deaths per annum (1, 2). *Mycobacterium bovis* causes tuberculosis in cattle, but it is also highly virulent in man. Leprosy, caused by *Mycobacterium leprae*, remains a major unresolved health problem in developing countries (3).

Infections by members of the *Mycobacterium avium intracellulare* complex cause disease in birds and in pigs and are among the most frequent opportunistic infections found in patients suffering from acquired immunodeficiency syndrome (AIDS) (4, 5). Further, the recent dramatic re-appearance of tuberculosis in developed countries and the appearance and propagation of drug resistant *M. tuberculosis* strains (6) underline the difficulty of controlling mycobacterial diseases.

Molecular characterisation of the various steps in the pathogenesis of mycobacterial diseases is fundamental to the development of optimised and rational therapeutic and prophylactic approaches to such diseases. The virulence carriers are often good antigens which can be used as candidates for vaccines. Despite the importance of mycobacterial infections, little is known about the basic molecular mechanisms involved in their pathogenesis (7).

One of the initial and crucial events in bacterial pathogenesis is adhesion of the micro-organism to its target cells. Mycobacteria exhibit tropism for pulmonary macrophages (8). However, since such micro-organisms are readily transmitted by aerosol, the first structures in the host which they encounter during infection are those of the respiratory epithelium. As a result, interactions with epithelial cells or with the extracellular matrix (ECM) during the initial and subsequent steps of pathogenesis can be important (9), although they have not yet been studied to any great extent.

Within the context of the present invention, the inventors have obtained a novel mycobacterial antigen involved in adhesion of mycobacteria to epithelial type host cells. It is a 28 kDa heparin binding haemagglutinin (HBHA) which has been obtained from culture supernatants prepared from cell walls of *Mycobacterium bovis* BCG and *Mycobacterium tuberculosis*. Immunoblot analysis using polyclonal and monoclonal antibodies have indicated that HBHA differs from proteins of the antigen 85 complex and represents a novel antigen. From this basic protein, the inventors have been able to evaluate and propose the development of a series of polypeptides which can be used for diagnosis, therapy and prophylaxis.

The invention thus provides a peptide sequence enabling mycobacteria to adhere to host cells, in particular epithelial cells. More particularly, the peptide sequence of the invention is characterized in that it is a mycobacterial heparin-binding haemagglutinin (HBHA) type antigen, in particular an antigen obtained from *Mycobacterium bovis* BCG or *Mycobacterium tuberculosis*.

In a preferred embodiment of the present invention, the peptide sequence is characterized in that it comprises the sequence corresponding to the sequence shown in FIG. 10 (SEQ ID No. 19), or any variant of that sequence which enables mycobacteria to adhere to host cells and obtained by addition, substitution or deletion of one or more amino acids of the sequence of FIG. 10 (SEQ ID No. 19).

Throughout the text, the term "polypeptide sequence" or "polypeptide" represents all or part of the sequence of FIG. 10, which itself represents the DNA and the HBHA protein as it is. The term "protein" designates the modified or non modified polypeptide sequence.

Preferably, the invention more particularly provides a peptide sequence comprising a region involved in interactions with sulphated glycoconjugates and in heparin binding. This peptide sequence is as follows:

KKAAPAKKAAPAKKAAPAKKAAAKKAPA-KKAAAKKKVTQK (SEQ ID No. 1).

The invention thus concerns a peptide sequence comprising the C-terminal portion of the sequence of FIG. 10 and more particularly the sequences comprising approximately the last 30 to 50 amino acids of the C-terminal portion of the sequence of FIG. 10. This region of the sequence of FIG. 10 is involved in the interaction of the protein with heparin, although a shorter sequence, in particular of about 10 to 20 amino acids, may be sufficient.

The inventors have also expressed the nucleotide sequence coding for the peptide sequence of the invention in *E. coli*. The polypeptide obtained has a lower molecular weight than that of the purified protein from *M. bovis* BCG or *M. tuberculosis*. These differences are the result of post-translational modifications which do not occur in *E. coli*.

The invention thus also provides a recombinant peptide sequence, characterized in that it enables mycobacteria to adhere to host cells. More particularly, the recombinant sequence of the present invention is the expression product of a nucleotide sequence coding for a peptide sequence enabling mycobacteria to adhere to host cells, in particular an antigenic sequence obtained from *M. bovis* BCG or *M. tuberculosis*, said recombinant sequence being, for example, the expression product of an *E. coli* strain transformed with a suitable nucleotide sequence.

The invention also relates to the use of one of the peptide sequences described above, whether recombinant or non recombinant, and more particularly in its native form for serological diagnosis of the presence of mycobacteria. The invention also provides an immunogen composition characterized in that it comprises one of the peptide sequences described above and to the use of that peptide sequence to prepare vaccines against mycobacterial infections, particularly infections caused by *M. bovis* or *M. tuberculosis*.

The inventors have also discovered that adhesion of mycobacteria to epithelial cells can be specifically inhibited by sulphated glucides. The invention thus concerns the use of a sulphated glucide to inhibit adhesion of mycobacteria to epithelial cells. Sulphated glucides of particular interest include heparin, chondroitin sulphate and dextran sulphate as well as their synthetic derivatives.

The inventors have also isolated the whole of the gene coding for HBHA from the DNA of *M. bovis* BCG. The invention thus provides a nucleotide sequence, characterized in that it codes for a peptide sequence enabling mycobacteria to adhere to host cells. More particularly, the nucleotide sequence of the invention codes for a mycobacterial heparin-binding haemagglutinin (HBHA) type antigen, in particular the peptide sequence of FIG. 10 or any portion of that peptide sequence enabling mycobacteria to adhere to host cells and obtained by addition, substitution or deletion of one or more amino acids from said peptide sequence.

The invention also provides a recombinant host cell, characterized in that it comprises one of the nucleotide sequences described above in its genome. In one preferred embodiment of the invention, the recombinant host cell is BCG, but not exclusively, for which expression vectors directly usable for developing recombinant BCG for use in man or animal have been developed.

BCG is used in therapy, more particularly in anti-cancer therapy, in particular against superficial cancers of the bladder. In this type of therapeutic application, a correlation between the adhesion ability of the BCG and its anti-tumoral power appears to exist. Within the context of the present invention, identification of the HBHA and cloning of its gene renders possible an increase in adhesion capacity via overexpression of the gene coding for HBHA.

The present invention will now be described with reference to the following Figures:

FIG. 1A is a graph illustrating an adhesion test carried out with CHO in the presence of increasing concentrations of D(+)galactose (black circles) or heparin (white circles) from pork intestinal mucosa.

FIG. 1B shows the effect of sulphated and non sulphated glucides on mycobacterial adhesion to CHO cells and to macrophages;

FIG. 4 shows the effect of sulphated glucides and non sulphated glucides on haemagglutinination induced by HBHA;

FIG. 5A is a graph illustrating the inhibition of adhesion of BCG to CHO cells by anti-HBHA monoclonal antibodies 3921E4;

FIG. 5B is a graph illustrating the inhibition of adhesion of BCG to CHO cells by anti-HBHA polyclonal antiserum;

FIG. 7 shows the nucleotide sequence (SEQ ID No. 17) and the amino acid sequence (SEQ ID Nos. 17 and 18) of a fragment of HBHA deduced from a PCR fragment of chromosomal BCG DNA;

FIG. 9 shows the sequencing strategy for the gene coding for HBHA;

FIG. 10 shows the DNA sequence of the BCG gene coding for HBHA (SEQ ID No. 19);

DETAILED DESCRIPTION OF THE INVENTION

Figure 2:
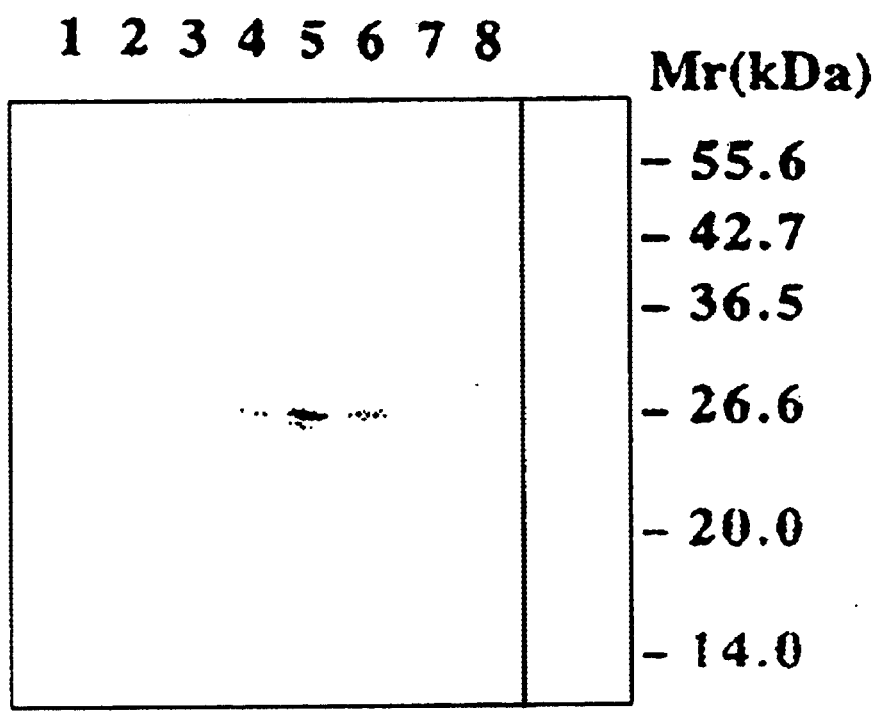
FIG. 2 shows data demonstrating purification of a heparin binding protein of *M. bovis* BCG.

Inhibition of Mycobacterial Adhesion to Epithelial Cells by Sulphated Glucides The invention concerns the use of sulphated glucides to inhibit adhesion of mycobacteria to epithelial cells. To demonstrate that mycobacteria can adhere via sulphated glucides, the inventors tested whether soluble sulphated polysaccharides were capable of reducing the adhesion of *M. bovis* BCG to epithelial cells.

*M. bovis* BCG (strain 1173P2, OMS, Stockholm, Sweden, passes 3 to 8) in exponential growth were labelled by cultivating the mycobacteria for three days in Sauton medium containing 5 $\mu$Ci/ml of [6-$^3$H]uracil (New England Nuclear, 24 Ci/mmole). The mycobacteria were then harvested by centrifugation (3000×g for 5 minutes), washed twice with a Dulbecco saline phosphate buffer (DPBS) and taken up into suspension in RPMI 1640 culture medium containing 300 mg/l of L-glutamine (GIBCO), free of foetal calf serum (RPMI).

The day before the adhesion test, the wells of 24-well tissue culture plates (Nunclon, Nunc, Denmark) were inoculated with $10^5$ extemporaneously cultivated cells from the ovaries of Chinese hamsters (CHO) (see FIG. 1A, and FIG. 1B, open bars) or J774A.1 macrophages (ATCC TIB67) (see FIG. 1B, speckled bars) taken up into suspension in 2 ml of RPMI with an added 10% (v/v) of decomplemented foetal calf serum (RPMI-FCS). Just before the test, the cells were washed three times with 2 ml of RPMI, and 1 ml of the mycobacterial suspension in RPMI was added to each well to obtain an infection multiplicity of 10 bacteria per eukaryote cell.

The adhesion test was carried out in the presence of increasing concentrations of D(+)galactose (Sigma) (see FIG. 1A, black circles) or heparin from pork intestinal mucosa ($M_r$ 6 kDa, Sigma) (see FIG. 1A, white circles), or with 20 $\mu$g/ml of the indicated glucides (Sigma) (see FIG. 1B). After 6 hours of incubation at 37° C. in an atmosphere containing 5% of $CO_2$, the cells were washed three times in 2 ml of DPBS, and finally lysed by adding 1 ml of distilled water containing 0.1% (w/v) of sodium deoxychlorate. The radioactivity associated with the cellular lysates was counted using a liquid scintillation counter (Beckman, model LS 6000SC). Residual adhesion was expressed as a percentage of the radioactive counts per minute with respect to the counts obtained in the absence of glucide. The data shown in FIGS. 1A and 1B represent the averages of four experiments, and show the error bars.

As shown in FIG. 1A, low concentrations of heparin substantially inhibited adhesion to CHO cells of BCG labelled with [$^3$H]uracil, while up to 100 $\mu$g/ml of galactose had no significant effect. Dextran sulphate, fucoidane and chondroitin sulphate could reduce adhesion, but no significant inhibition was observed with non sulphated mannose or dextran, even at the highest concentrations tested (1 mg/ml).

These results lead to the proposal that mycobacteria have a major sulphated glucide binding adhesin on their surface. However, as adhesion inhibition did not exceed 70%, other components are very probably involved in this process. Interestingly, interactions of BCG with J774A.1 macrophages were not affected by sulphated glucides, nor by non sulphated sugars (FIG. 1B), even at concentrations of up to 1 mg/ml (results not shown). This is in agreement with previous reports naming receptors of the CR1, CR3 and CR4 complement as mycobacterial ligands on the surface of sanguine monocytes and alveolar macrophages (10–12).

Purification of a Heparin Binding Protein Present in M. Bovis BCG and M. Tuberculosis The invention concerns a peptide sequence enabling mycobacteria to adhere to host cells. Inhibition of adhesion of BCG to epithelial cells by sulphated sugars would already suggest that mycobacteria express an adhesin which interacts with sulphated glycoconjugates, such as sulphated glycoproteins or glycolipids present on the surface of the host cells. To identify the adhesins in question, BCG culture supernatants were fractionated by chromatography on heparin-sepharose.

*M. bovis* BCG were cultivated at 37° C. in static cultures in 175 $cm^3$ Roux flasks (Falcon, Becton-Dickinson) containing approximately 150 ml of Sauton medium. In the stationary phase, the cultures were centrifuged (10000×g for 20 minutes), and 500 ml of supernatant was loaded onto a heparin-sepharose CL-6B column (1×5 cm) (Pharmacia) equilibrated with DPBS. The column was then washed with 100 ml of DPBS, and the retained molecules were eluted by a linear gradient of NaCl, 0–500 mM, in 100 ml of DPBS. The flow rate during all of the steps was kept at 1.5 ml/min, and the absorbance of the eluent, which was harvested in 1 ml fractions, was continuously monitored at 280 nm. These fractions were analysed by SDS-PAGE (13) using a 12% gel followed by staining with Coomassie Brilliant Blue R-250.

The fractions analysed after the start of the gradient are shown in tracks 1–8 of FIG. 2. The right hand tracks show the heparin binding protein purified from a preparation of *M. bovis* BCG cell walls. The size of the markers $M_r$, expressed in kDa, are given in the right hand margin.

As shown in FIG. 2, a single protein of 28 kDa was eluted at approximately 350 mM of NaCl. The interaction between this protein and heparin was dependent on the sugar sulphatation as that could also be purified using dextran sulphate beads, but not with dextran beads (not shown). The same heparin binding protein was also purified from *M. tuberculosis* culture filtrates.

The production of two similar heparin binding proteins from two different mycobacterial strains confirms that proteins of this type are present in the majority of pathogenic mycobacterial strains. Homology percentages of less than 100% could lead to structural differences, although the fundamental properties of these proteins are not affected. The invention thus also concerns heparin binding proteins with a structure related to the isolated protein and which can be obtained using its properties of adhesion to sulphated glucides. These proteins can be distinguished from the protein of the invention by additions, substitutions and deletions of amino acids without that substantially affecting their properties of adhesion to epithelial cells.

Localisation of the Heparin Binding Mycobacterial Protein on the Cell Surface In order to determine whether this protein is a strictly secreted protein or if it could be associated with the mycobacterial surface, cell wall fractions were prepared from BCG, then chromatographed on heparin-sepharose.

To prepare the cell walls, mycobacteria were cultivated in 2 liters of Sauton medium or in Long synthetic medium (Quality Biological Inc., Gaithersburg, Md.) for 12 to 14 days. The bacteria were then harvested by centrifugation, washed once with DPBS containing 0.05% (v/v) of Tween 80 (DPBS/Tw), taken up into suspension in 100 ml of DPBS/Tw and heated to 80° C. for 1 hour. The bacteria were centrifuged at 13000×g for 20 minutes, washed with DPBS/Tw, taken up into suspension in 25 ml of DPBS/Tw containing 5 nM of protease inhibitor AEBSF, RNase A and DNase I, sonically lysed intermittently for 25 minutes, then centrifuged at 13000×g for 20 minutes. This step was repeated and the supernatants were combined and centrifuged at 34000×g for 3 hours at 4° C. The residue was discarded and the final supernatant was diluted 1:2 in DPBS and chromatographed on CL-6B heparin-sepharose.

As shown in FIG. 2, the 28 kDa heparin binding protein was also present in these preparations, confirming that it was associated with the surface. It was also present in cell wall fractions of *M. tuberculosis* and in tuberculine preparations (purified antigenic proteinic derivative for cutireaction) derived from *M. tuberculosis.*

Haemagglutinination Activity of the Mycobacterial Heparin Binding Protein

The capacity of bacterial adhesins to agglutinate erythrocytes is often used as a model to study microbial binding such as that of lectins to the receptor in eukaryotic cells. The inventors thus tested the purified heparin binding protein for its capacity to agglutinate erythrocytes.

The haemagglutinination activity of the purified heparin binding protein in culture supernatants was measured in U microtitration plates (Falcon) in the absence or in the presence of heparin (FIG. 4, black squares) from pork intestinal mucosa, dextran sulphate (FIG. 4, black circles) or dextran (FIG. 4, white circles) in concentrations of 0 to 50 μg/ml. Standard tests contained 70 μl of a fresh suspension of rabbit erythrocytes prepared in DPBS and 70 μl of purified HBHA corresponding to 1 μg of protein. The amount of haemagglutinination was read after 5 hours of incubation at room temperature. The data represent the averages over four experiments, and the error bars are shown.

Less than 0.1 μg of purified protein was able to induce haemagglutinination of rabbit erythrocytes, but not of human, sheep, goose or chicken erythrocytes (data not shown). For this reason, the inventors designated this protein as being the heparin binding haemagglutinin (HBHA). Haemagglutinination induced by HBHA was inhibited by heparin or by dextran sulphate, but not by dextran (see FIG. 4), which is similar to the results obtained in the tests for adhesion of mycobacteria to CHO cells. The haemagglutinination activity was heat sensitive in that incubation of the protein for 60 minutes at 80° C. destroyed haemagglutinination.

Inhibition of Haemagglutinination Activities and Adhesion Originating from Mediation by HBHA, by Specific Polyclonal and Monoclonal Antibodies Since mycobacterial adhesion to epithelial cells is inhibited by sulphated glucides, and a 28 kDa protein was purified by heparin-sepharose chromatography, it was important to establish whether mycobacterial adhesion originated from mediation by HBHA.

As a result, anti-HBHA rat polyclonal antibodies were prepared as follows: 200 μg of purified BCG HBHA underwent preparative electrophoresis on a 15% polyacrylamide gel in the presence of SDS, then electro-transferred to a nitrocellulose membrane. After rapid staining with xylidene red, the bands corresponding to HBHA were excised with care, cut into small squares and briefly sonically lysed in 1.5 ml of sterile PBS. After adding 1 ml of a monophosphoryl-lipid A solution (MPL+TDM System Adjuvant, Sigma Chemical Co., St. Louis, Mo.) prepared in accordance with the manufacturer's recommendations, two Fischer rats were each immunised with 1 ml of the antigen suspension. For each immunisation, 400 µl was administered intraperitoneally and two times 300 µl subcutaneously. The animals received repeat immunisations in the same manner with the same quantity of antigen one month later, and the serum was recovered 3 weeks after that repetition.

The BCG was labelled with [6-$^3$H]uracil as described above. Approximately 4×10$^6$ radiolabelled BCG were taken up into suspension in 1 ml of PBS and pre-incubated with the indicated volumes of ascetic liquids of monoclonal antibodies 3921E4 (14) anti-HBHA (FIG. 5A), or with 250 µl of rat anti-HBHA polyclonal antiserum (immunitary serum, FIG. 5B) or naive serum (FIG. 5B, control serum) for 30 minutes, at room temperature. The hybridoma producing the 3921E4 anti-HBHA monoclonal antibodies was deposited on Jun. 25, 2002, at the Collection Nationale de Cultures de Microorganismes (Institut Pasteur, 25 rue du Docteur Roux, Paris 15, France) under the registration number CNCM I-2900. The bacterial suspensions were then washed three times with 2 ml of DPBS to eliminate the non bound antibodies, then used in the CHO cell adhesion test in an infection multiplicity of 10, as described above.

As shown in FIG. 5, adhesion of BCG to CHO cells was inhibited substantially in a dose-dependent manner by the presence of anti-HBHA antibodies. The ascites liquids containing the non pertinent monoclonal antibodies or naive antiserums had no effect. These observations indicate that adhesion of mycobacteria to epithelial cells originates in part through the mediation of HBHA.

HBHA Characteristics Study

Since the size of this protein is close to that of fibronectin binding proteins in the antigen 85 complex (15), Western blot analyses were used to determine whether they were related.

Purified heparin binding protein from a preparation of *M. bovis* BCG cell wall (FIG. 3, track 1) or culture supernatant (track 2) was compared with purified antigen 85 complex (track 3) by immunoblot analysis (panels A, B, C) and staining with Coomassie Blue (panel D) after SDS-PAGE. Immunoblot analysis was carried out using polyclonal antibodies directed against the purified heparin binding protein (panel A), the monoclonal antibody 4057D2 (panel B) or polyclonal antibodies directed against antigen complex 85 (panel C). The hybridoma producing the 4057D2 anti-HBHA monoclonal antibody was deposited on Jun. 25, 2002, at the Collection Nationale de Cultures de Microorganismes (see above) under the registration number CNCM I-2901. Tracks 1 and 2 of panels A, B and C contained 2 µg of purified protein, tracks 3 of panels A, B and C contained 7 µg of purified protein, and tracks 2 and 3 of panel D contained 4 µg and 15 µg of purified protein respectively. The size of labels M, is shown in the margins.

Figure 3:
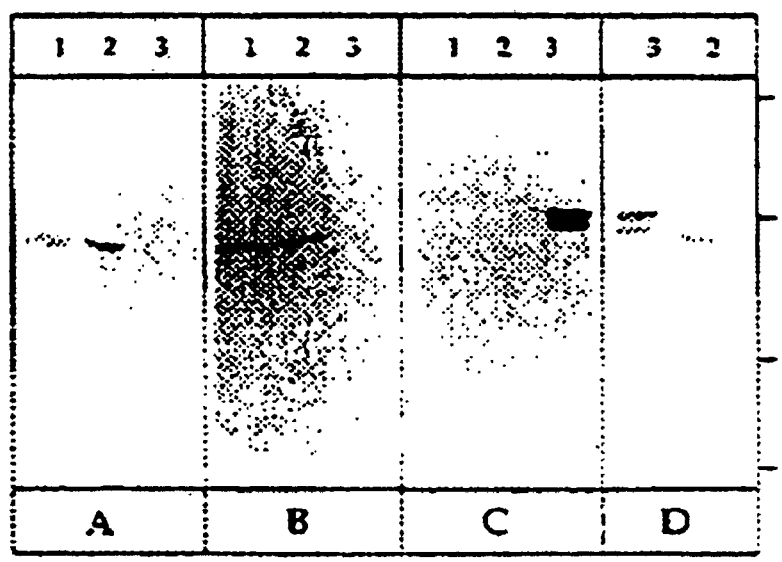
FIG. 3 shows a comparison of the heparin binding protein of *M. bovis* with the antigen 85 complex.

FIG. 3 demonstrates that polyclonal antibodies directed against the 28 kDa purified BCG heparin binding protein did not recognise purified antigen 85 complex proteins. In contrast, polyclonal and monoclonal antibodies (not shown) directed against the BCG antigen 85 complex had not succeeded in recognising the heparin binding protein, which implies that the proteins are distinct. This result is also supported by the different migration profiles for these proteins during SDS-PAGE (FIG. 3, panel D).

The N-terminal amino acids of the purified heparin binding proteins of H37Ra *M. tuberculosis* and of BCG were sequenced. This was accomplished by subjecting 25 µg of HBHA to polyacrylamide-SDS gel electrophoresis using a 15% polyacrylamide gel. After electrophoresis, the material was transferred to a PVDF membrane (ProBloft, ABI) by electroblotting. After staining with Coomassie blue, the band corresponding to HBHA was excised and underwent automatised Edman degradation. The first 16 amino acids were Ala-Glu-Asn-Ser-Asn-Ile-Asp-Asp-Ile-Lys-Ala-Pro-Leu-Leu-Ala-Ala (SEQ ID No. 20 from amino acid positions 2 to 17). The first 16 amino acids in the BCG heparin binding protein were also determined and proved to be identical to those of *M. tuberculosis*. A similarity search in protein databases showed that the heparin binding protein had not been identified before, and that it thus represents a novel mycobacterial protein. Further, the first 16 amino acids did not exhibit any significant sequence similarity with other known protein sequences.

Cloning of the BCG Gene Coding for HBHA

To clone the gene coding for HBHA, firstly the N-terminal sequences of internal HBHA fragments were determined. To this end, purified HBHA underwent electrophoresis as described above. After electrophoresis, the protein was digested with trypsin inside the gel. The resulting peptides were then isolated by reverse phase HPLC, and then underwent Edman degradation. Four peptides enabled the sequence to be determined:

Peptide Lys-Ala-Glu-Gly-Tyr-Leu-Glu-Ala-Ala-Thr (SEQ ID No. 2)

S1441:

Peptide Xxx-Glu-Gly-Tyr-Val-Asp-Gln-Ala-Val-Glu-Leu-Thr-Gln-

S1443: Glu-Ala-Leu-Gly-Lys (SEQ ID No. 3)

Peptide Xxx-Gln-Glu-Xxx-Leu-Pro-Glu-Xxx-Leu (SEQ ID No. 4)

S1446:

Peptide Phe-Thr-Ala-Glu-Glu-Leu-Arg (SEQ ID No. 5)

S1447:

The sequence of two pairs of oligonucleotides was derived from the internal HBHA peptide sequences. The generally high G+C content in the mycobacterial DNA has led the inventors to favour G or C in the third position of the codons (wobble). The first pair of oligonucleotides originated from the S1441 peptide and had the following sequences: 5'AAG GC(G/C) GAG GG(G/C) TAC CT 3' (oligo S1441) (SEQ ID No. 6) and 5'AGG TA (G/C) CCC TC(G/C) GCC TT 3' (reverse oligo S1441) (SEQ ID No. 7). The second pair of oligonucleotides originated from the S1443 peptide and had the following sequences: 5'GAC CAG GC(G/C) GT (G/C) GAG CT 3' (oligo S1443) (SEQ ID No. 8) and 5' AGC TC (G/C) AC(G/C) GCC TGG TC 3' (reverse oligo S1443) (SEQ ID No. 9).

The chromosomal BCG DNA was extracted as described by Kremer et al (16). Polymerisation chain reactions (PCR) using 50 ng of chromosomal BCG DNA and 1 µg of either reverse S1441 and S1443, or reverse oligo S1443 and S1441, were carried out at a hybridization temperature of 50° C. with 30 PCR cycles. Only the PCR carried out with the reverse S1441 and S1443 oligonucleotides produced a specific amplified DNA fragment of approximately 150 bp.

This amplified fragment was again observed when the hybridisation temperature was increased to 57° C.

The amplified fragment was inserted into the HindII site of pUC18 (Boehringer, Mannheim) and introduced into *Escherichia coli* XLI-Blue (New England Biolabs). The amount of recombinant *E. coli* plasmid was then analysed using standard methods (17) and the plasmid containing the expected fragment was designated pClone5.

After purification by chromatography on a Nucleobond AX column (Macherey-Nagel) following the instructions of the supplier, a bicatenary DNA fragment of approximately 150 bp was sequenced using the dideoxyribonucleotide chain elongation termination method using [alpha-$^{35}$S]dCTP (1000 Ci/mole; Amersham) and the T7 sequencing kit (Pharmacia) following the instructions of the manufacturer. The sequence obtained is shown in FIG. 7 in which the sequence of two oligonucleotides used for the PCR is underlined. The sequence of amino acids deduced from the DNA sequence was found to correspond to the sequence of amino acids determined for peptides S1441 and S1443. This indicates that the amplified PCR fragment corresponded to an internal portion of the BCG gene coding for HBHA.

Figure 8:
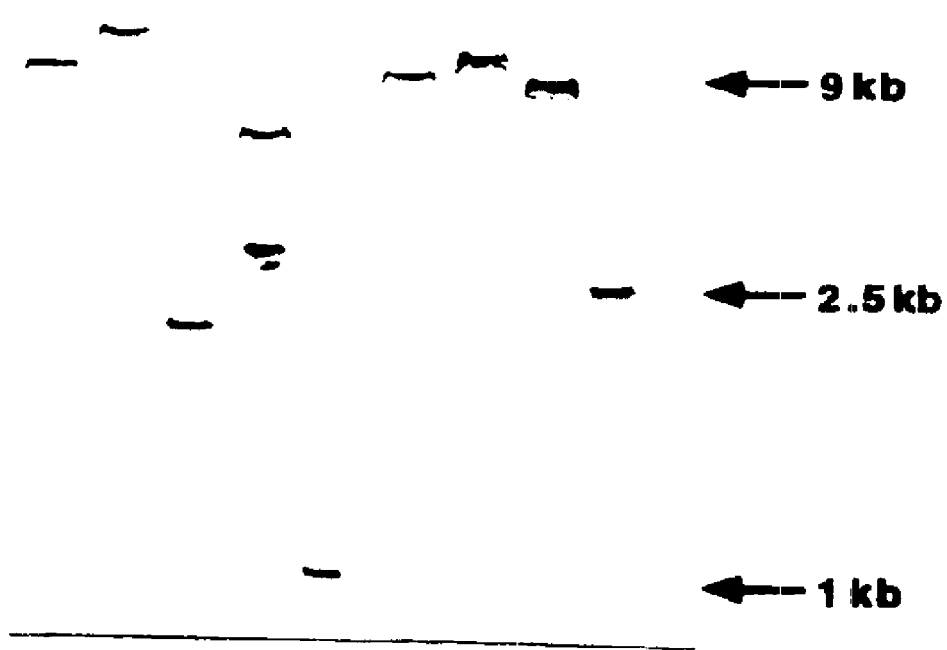
FIG. 8 shows a Southern blot analysis of chromosomal BCG DNA.

In order to clone the whole of the gene coding for HBHA, the 150 bp fragment of pClone5 was excised by digestion with restriction enzymes BamHI and HindIII. The fragment was then purified by electrophoresis on a 7% polyacrylamide gel and excised from the gel by electro-elution. The purified fragment was labelled with digoxigenin using the DIG (Boehringer) DNA detection and labelling kit as recommended by the manufacturer. The labelled fragment was then used in Southern Blot experiments to probe the chromosomal BCG DNA digested with BamHI (FIG. 8, track 1), EcoRI (FIG. 8, track 2), PstI (FIG. 8, track 3), SmaI (FIG. 8, track 4), AccI (FIG. 8, track 5), NcoI (FIG. 8, track 6), NotI (FIG. 8, track 7), SacI (FIG. 8, track 8) or SphI (FIG. 8, track 9), which underwent electrophoresis on agarose and was transferred to a nylon membrane. The membrane was then probed with the approximately 150 bp BamHI/HindIII fragment from pClone5. The marker sizes are shown in the right hand margin. Southern blot analyses were carried out using standard protocols (17). As shown in FIG. 8, digestion with chromosomal BCG DNA resulted in a unique fragment of about 2.5 kb which hybridised with the probe.

2.3 to 2.7 kb SphI restriction fragments from chromosomal BCG DNA were then purified by preparative electrophoresis and electro-elution, and inserted in the SphI site of pUC 18. Recombinant plasmids were used to transform *E. coli* XLI-Blue. White colonies cultivated on gelose LB (17) with added ampicillin (150 µg/ml), isopropyl-thiogalactopyrannoside (IPTG, 40 µg/ml) and X-gal (40 µg/ml) were analysed by hybridisation on colonies using the probe labelled with digoxigenin. Of approximately 300 colonies which were analysed, one had hybridised with the probe. Restriction analysis of the plasmid isolated from these clones had indicated that it contained a SphI fragment of 2.5 kb which had hybridised with the probe in Southern blot.

Analysis of the Sequence of the BCG Gene Coding for HBHA

The gene coding for HBHA contained in the 2.5 kb SphI fragment was sequenced using the dideoxyribonucleotide chain elongation termination method described above. The synthetic oligonucleotide sequences used for sequencing are shown in Table 1, and the sequencing strategy is shown in FIG. 9. The cloned 2.5 kb SphI fragment is shown by the black line. The dotted lines represent the DNA vector. The bold arrows represent the open reading frame of HBHA. The fine arrows indicate the direction and length of the DNA fragment sequenced for each oligonucleotide indicated above its respective arrow.

TABLE I

Oligonucleotides used for sequencing the gene coding for HBHA.

| Name of oligonucleotide | Sequence |
|---|---|
| HBHA Seq1 | 5'AGC CGG TAC AAC GAG CTG GTC 3' (SEQ ID No. 10) |
| HBHA Seq1inv | 5'GAC CAG CTC GTT GTA CCG GCT 3' (SEQ ID No. 11) |
| HBHA Seq2 | 5'CAT CCA ACA CGT CGA CTC C 3' (SEQ ID No. 12) |
| HBHA Seq3 | 5'TTG ATG TCA TCA ATG TTC G 3' (SEQ ID No. 13) |
| HBHA Seq4 | 5'CGT GGA CCA GGC GGT GGA G 3'(SEQ ID No. 14) |
| HBHA Seq5 | 5'GAC GAT CAG GAG GTT TCC CCG 3'(SEQ ID No.15) |
| Reverse primer | 5'AGC GGA TAA CAA TTT CAC ACA GGA 3' (SEQ ID No. 16) |

The whole of the gene coding for HBHA was localised inside the 2.5 kb SphI fragment at one end of the fragment, and it was completely sequenced from two strands.

The nucleotide sequence and the derived protein sequence are shown in FIG. 10. The open reading frame is shown between nucleotides 331 and 927. The first 16 codons after the optional start codon ATG 331/333 are translated into an amino acid sequence which is identical to that determined after N-terminal sequencing of the purified HBHA protein. Upstream of the optional start codon, at residues 331–333, a stop codon TAG is found in phase at positions 310–312. This strongly suggests that the HBHA open reading frame contains no sequences coding for the conventional signal peptide, and 331/333 thus probably represents the start codon. This is supported by the presence of a putative ribosome binding site AGGAA which is found 10 to 6 nucleotides upstream of the start codon.

The invention also concerns any variant of the sequences described above obtained by addition, substitution or deletion of one or more amino acids without substantially modifying the properties of the region of interest. Among the envisaged modifications are silent mutations in the nucleotide sequences which do not modify the peptide sequence of the protein or the fragment of interest, also conservative mutations which consist of substituting one or more amino acids with the same functional characteristics as the amino acid of the native sequence. Additions or deletions of amino acids without substantially modifying the properties of the regions of interest also form part of the invention. Certain residues can be eliminated or modified by expressing a modified gene in this way in *E. coli* as described for the complete gene. If this protein binds heparin with the same affinity as whole HBHA, this signifies that the repeat sequences are not involved in that binding. In contrast, if the modified protein loses the capacity to interact with heparin, the modified region of the protein plays a role in that interaction.

Expression of the BCG HBHA Gene in *Escherichia coli*

The invention also concerns a recombinant host cell, characterized in that it comprises one of the nucleotide sequences described above in its genome. More particularly, the invention concerns the transformation of host cells such as *E. coli* with one of the nucleotide sequences of the invention to produce all or part of the HBHA protein. The bacterial strain to be transformed can comprise the complete sequence coding for HBHA appearing in FIG. 10 or the sequence which may be involved in interactions with sulphated glycoconjugates or the C-terminal portion of that sequence. By way of example, the complete gene coding for BCG HBHA was introduced and expressed in *E. coli*.

In order to produce BCG HBHA in *Escherichia coli*, the plasmid derived from pUC18 which contained the 2.5 kb SphI fragment comprising the BCG HBHA gene was simultaneously restricted with NcoI and KpnI. The 705 base pair fragment from this double restriction was purified by electro-elution after migration in a 1% agarose gel using standard procedures (17) and finally cloned in the expression vector pKK388-1 (Clontech, Palo Alto, Calif., UA) previously restricted with NcoI and KpnI. The recombinant plasmid was then introduced into *E. coli* XL1-Blue using conventional transformation techniques (17).

Phenotype analysis of the strain carrying this expression plasmid was carried out by cultivating it in a liquid LB medium and stimulating the production of recombinant HBHA by adding isopropylthio-galctopyranoside (IPTG) using standard methods (17). Practically, two cultures in 500 ml erlenmeyer flasks each containing 100 ml of liquid LB medium supplemented with ampicillin in an amount of 150 μg/ml were respectively inoculated with 4 ml of *E. coli* XL1-Blue preculture containing the HBHA expression plasmid or plasmid pKK388-1 representing the control culture. The growth in the two cultures was monitored by measuring the optical density at 600 nm. When this reached 0.6, IPTG was added to the cultures in an amount of 1 mM final and culture was continued for 4 hours. Culture samples were removed before adding the IPTG and at the end of the 4 hours of culture in the presence of an inducer for analysis by polyacrylamide gel electrophoresis and by immunoblotting the production of recombinant HBHA.

Figure 11:
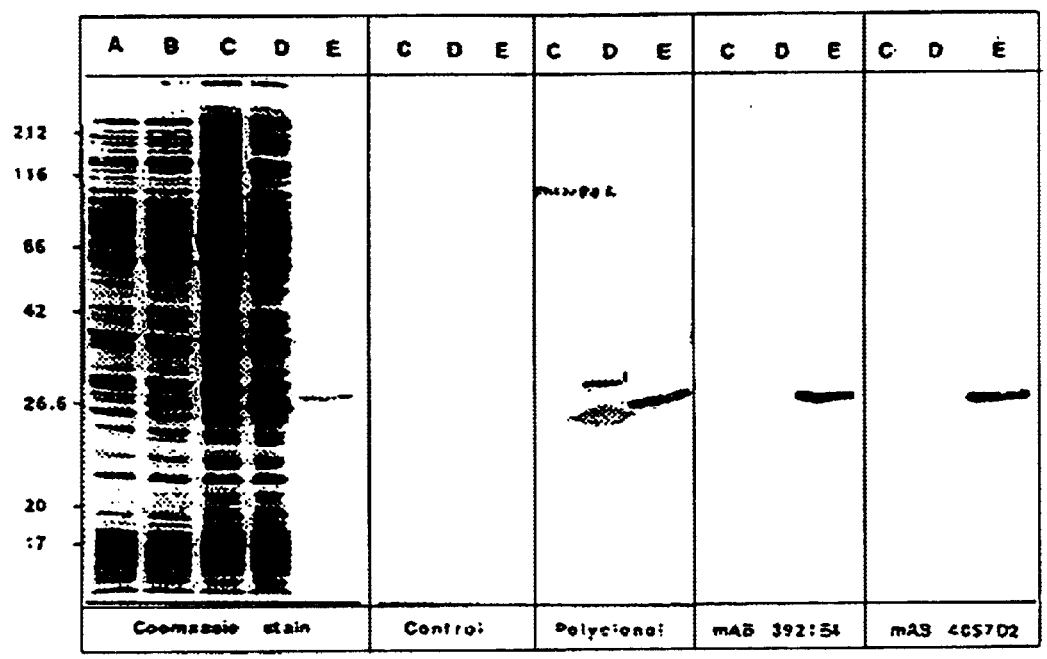
FIG. 11 shows a polyacrylamide gel electrophoresis and immunoblot analysis of the expression of HBHA in *E. Coli*.

The results of these different analyses are shown in FIG. 11.

Tracks A and B represent total lysates before introducing *E. coli* XL1-Blue respectively transformed with pKK388-1 and the derivative of pKK388-1 containing the gene coding for HBHA. Tracks C and D represent total lysates after IPTG induction of *E. coli* XL-1-Blue respectively transformed with pKK388-1 and the derivative of pKK388-1 containing the gene coding for HBHA. Tracks E contained 1 μg of purified HBHA from BCG walls. From left to right, the different panels respectively represent staining of the polyacrylamide gel with Coomassie blue R-250 and immunoblots probed with a control murine serum, a murine serum directed against BCG HBHA, the murine monoclonal antibody 3921E4 and the murine monoclonal antibody 4057D2. The reference molecular weights are noted to the left of the panel showing staining of the polyacrylamide gel with Coomassie blue.

Analysis of the polyacrylamide gel stained with Coomassie blue shows the synthesis of a polypeptide of about 27 kDa in *E. coli* XL-1 Blue carrying the HBHA expression vector and derepressed by IPTG. This polypeptide, recognised in immunoblotting by a murine antiserum directed against the purified HBHA protein of a BCG culture supernatant, was not produced by *E. coli* XL-1 Blue carrying the pKK388-1 vector with no insert, showing that its synthesis depends on the cloned BCG DNA sequence in the expression vector. As this is also the sequence coding for the BCG HBHA, it was surprising to observe that the recombinant polypeptide had an apparent molecular weight which was lower than that of the purified BCG HBHA and which was 28 kDa in the gel system under consideration.

The invention thus also concerns a recombinant peptide sequence characterized in that it enables mycobacteria to adhere to host cells. More particularly, the invention concerns a peptide sequence comprising a polypeptide of about 27 kDa recognized by the monoclonal antibody 3921E4 (14) and not recognized by the monoclonal antibody 4057D2 (14). Preferably, the recombinant peptide sequence of the invention is the expression product of a strain of *E. coli* transformed with one of the nucleotide sequences described above and coding for a peptide sequence enabling mycobacteria to adhere to host cells, more particularly a nucleotide sequence obtained from *M. bovis* BCG or *M. tuberculosis*. The invention also concerns any variation in this recombinant peptide sequence obtained by addition, substitution or deletion of one or more nucleotides such that the transformed strain produces a different peptide sequence but which possesses the property of adhering to host cells, and more particularly to epithelial cells.

Since the molecular weight of the HBHA deduced from the gene sequence is significantly lower than its apparent molecular weight observed after electrophoretic migration and that difference is the result of post-translational modifications of HBHA, these modifications did not occur in *E. coli*. This conclusion is supported by the fact that we observed a differential immuno-reactivity for recombinant HBHA with the two monoclonal antibodies 3921 E4 and 4057D2. While the two monoclonal antibodies recognise purified BCG HBHA in an equivalent manner on immunoblotting, only 3921 E4 was immunoreactive with recombinant HBHA produced in *E. coli*. This observation firstly shows that the epitopes of these two monoclonal antibodies are different and that the epitope recognised by 4057D2 on HBHA is no longer present when the latter is produced in *E. coli*, since it is localised on a molecular element resulting from a post-translational modification not carried out in *E. coli*.

This post-translational modification is a glycosylation since it has already been demonstrated that the saccharide portion of a glycoprotein can be immunogenic. The saccharide moiety is highly immunogenic since immunoblot analysis using anti-HBHA murine serum gave rise to a weaker signal with recombinant HBHA than with that observed with purified BCG HBHA. This observation is all the more telling since the quantity of recombinant HBHA used in this analysis was much larger than that of natural HBHA, as shown by the Coomassie blue staining of the polyacrylamide gel. Further, since the immunoreactivity of 3921E4 was close to that observed with murine serum, the epitope recognised by this monoclonal antibody is thus partially dependent on the suspected post-translational modification.

A number of experimental approaches have been envisaged to elucidate the exact nature of this post-translational modification. Firstly, purified HBHA from BCG is subjected to the action of different endoglycosidases or exoglycosidases in order to see whether the apparent molecular weight of this protein reduces after the action of these enzymes. A more rapid electrophoretic migration observed after digestion with one or more of those enzymes gives direct information about the chemical nature of the saccharide modification. In parallel, BCG cultures in the presence of glycosylation inhibitors (e.g., tunicamycin which inhibits N-glycosylation in gram-positive bacteria) constitute an interesting approach to elucidating the nature of the post-translational modifications of the HBHA.

Identification of the Heparin Binding Site of HBHA

As it has been demonstrated that HBHA plays a direct role in the interaction between BCG and epithelial cells, an interaction which can be inhibited by heparin, it is important to identify the region which is involved in the interaction of BCG with epithelial cells via sulphated polysaccharides.

HBHA produced in the recombinant form by *E. coli* is the object of proteolysis affecting its carboxyterminal extremity and involving a reduction in heparin affinity.

HBHA produced in *E. coli* WL1 Blue accumulates in the cytoplasm but remains soluble since sonic lysing of colibacilli followed by clarifying centrifugation (10000 g for 15 minutes) placed the whole of the HBHA detectable by immunoblot in the soluble fraction of the lysate. When the latter was incubated at room temperature, the recombinant HBHA degraded rapidly until at the end of an incubation period of 2 hours, its apparent molecular weight had dropped from 27 kDa to 19 kDa. The 19 kDa form which was not recognised by the monoclonal antibody 3921 E4 showed, however, good resistance to subsequent degradation since this form remained stable after a period of 18 hours incubation at room temperature. Since the degradation of recombinant HBHA could be stopped by adding 1 mM of native AEBSF which is a serine protease inhibitor, it is probable that this degradation was the result of proteolysis. It should be noted that native HBHA incubated in an *E. coli* XL-1 Blue lysate did not undergo similar degradation, thus suggesting that the post-translational modification in native HBHA endows it with resistance against the proteolysis observed with recombinant HBHA.

Chromatographic analysis on heparin-sepharose of a clarified sonicate of *E. coli* XL-1 Blue producing recombinant HBHA and supplemented with 1 mM of AEBSF showed that recombinant HBHA binds heparin with the same affinity as native HBHA since it eluted at 350 mM of NaCl in PBS. In contrast, HBHA degraded to a 19 kDa polypeptide no longer bound heparin which shows that the cleaved portion is indispensable in recognising sulphated polysaccharides. Recombinant HBHA purified on heparin-sepharose was also shown to be incapable of agglutinating rabbit erythrocytes. These observations show that post-translational modification of HBHA is not involved in its heparin binding activity but it is important for its haemagglutinination activity.

Analysis of recombinant HBHA by immobilised heparin matrix chromatography also showed itself to be of interest for mapping the protein domain involved in heparin recognition (the heparin binding site). Three forms of recombinant HBHA with molecular weights of 27, 26 and 25 kDa were eluted by a linear gradient of NaCl varying from 0 to 500 mM and applied to the washing buffer for the column (PBS). The 26 and 25 kDa forms, degradation products of the complete 27 kDa recombinant protein, eluted at about 310 and 280 mM NaCl respectively. Since the two forms had a low affinity for heparin compared with the complete recombinant protein, it was important to know the region where the truncations occurred. To this end, the amino-terminal extremities of the three purified forms on heparin-sepharose were microsequenced. Analysis of the first 10 amino acids showed that the 3 molecular species had the same sequence which was identical to the amino-terminal sequence of the purified HBHA from BCG walls. This observation thus shows that recombinant HBHA degrades by successive carboxy-terminal cleavages. These cleavages, along with a low affinity for heparin, show that the carboxy-terminal amino acids of HBHA are directly implicated in recognising sulphated polysaccharides. The large amount of lysines in the carboxy-terminal repeat zones of HBHA also argue for an electrostatic interaction between the positive charges on the lysines and the negative charges carried by the sulphated residues of the heparin.

The role of lysines in protein-sulphated sugar interactions has been documented elsewhere (18).

The 19 kDa form observed after proteolysis of recombinant HBHA could thus correspond to an HBHA which has lost its carboxy-terminal repeat sequences corresponding to a loss of 39 amino acids. In this hypothesis, the polypeptide chain of HBHA would lose a weight of about 3.8 kDa and would thus reduce from 21.3 to 17.5 kDa. The apparent molecular weight of recombinant HBHA after proteolysis in an *E. coli* XL-1 Blue lysate is completely compatible with this hypothesis. It is also interesting to note that the aberrant electrophoretic migration of HBHA is attributed to its carboxy-terminal repeat sequences, which is no longer observed with the degraded 19 kDa form which no longer binds heparin. This latter observation thus reinforces the hypothesis that the 19 kDa recombinant HBHA would correspond to an HBHA which has lost its carboxy-terminal repeat sequences. Since the monoclonal 3921E4 antibody no longer recognises the 19 kDa recombinant HBHA, this suggests that its epitope is localised in the carboxy-terminal repeat sequences.

Immune Reactivity Towards HBHA by Antisera from Tuberculosis Patients

In order to find out whether HBHA is capable of inducing an immune response in man, immuno blot analyses were carried out using purified HBHA and human antisera from tuberculosis patients. Five micrograms of the protein underwent electrophoresis using a 15% polyacrylamide-SDS gel, then were transferred to nitrocellulose membranes subsequently probed with sera diluted 100 fold originating from 7 different patients suffering from evolutive tuberculosis (see FIG. 6, tracks 3A at 493) (track 1, purified HBHA, track 2, non pertinent protein), also the serum from a healthy subject (control track). The left hand tracks contained purified proteins (tracks 1 and 2) and the molecular weight markers (see PM) were stained with Coomassie blue after SDS-PAGE.

Figure 6:
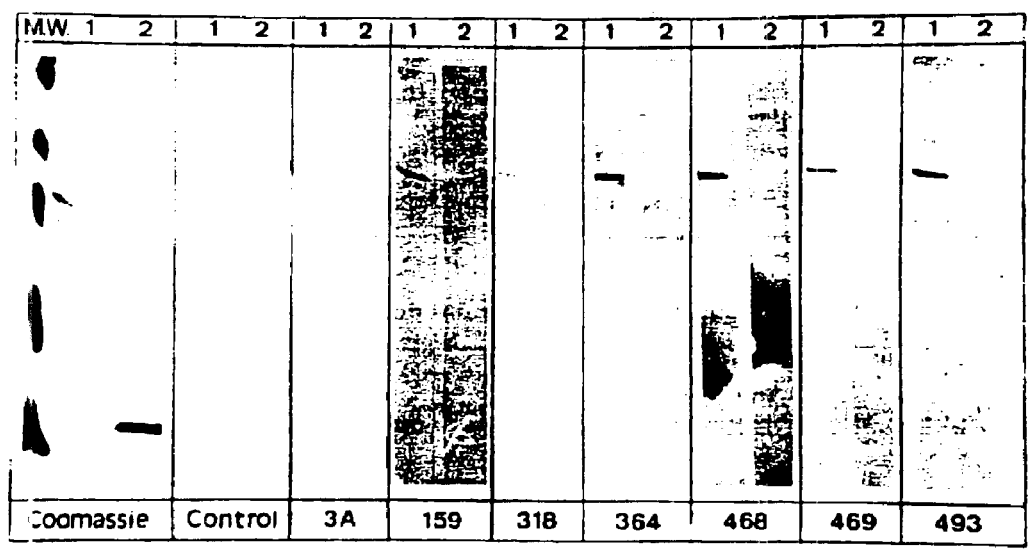
FIG. 6 shows immunoblot analyses carried out with tuberculous anti-sera.

The results shown in FIG. 6 show that all of the serums from tuberculosis patients contained anti-HBHA antibodies, while the serum from a healthy individual contained none of those antibodies. These results indicate that HBHA exposed on the surface is immunogenic during evolution of human tuberculosis and the presence of anti-HBHA antibodies enables the presence of mycobacterial infections to be determined.

The post-translational modification carried by native HBHA is a major antigenic determinant in patients with tuberculosis:

The recombinant HBHA produced by *E. coli* was analysed by immunoblot using the sera from patients with tuberculosis. Compared with the detection signals obtained with native HBHA, these immunological reactants only slightly recognised the recombinant protein, indicating that post-translational modification of the HBHA carried one or more major epitopes. These sera were proved to be incapable of detecting the 19 kDa recombinant HBHA.

The invention thus concerns the use of a peptide sequence or a protein of the invention, in particular one or more immunogenic regions of this sequence or protein, in the diagnosis of mycobacterial infections, in particular by showing the presence of anti-HBHA antibodies in the biological fluids. In general, a peptide sequence or the protein or a recombinant polypeptide, preferably modified in accordance with the invention, is bonded to a support and incubated with the biological fluids suspected of containing anti-HBHA antibodies. The anti-HBHA antibodies bonded to the polypeptide of the invention are then revealed either, for example, with labelled antibodies directed against the anti-HBHA antibodies, or with non labelled antibodies directed against the anti-HBHA antibodies and antibodies labelled, for example, with a peroxidase or alkaline phosphatase type enzyme, or biotin directed against non labelled antibodies.

In detail, the complete protein or a recombinant polypeptide of the invention can be used but one or more immunogenic regions of that protein can be used which can be determined by epitope mapping techniques which are well known to the skilled person. As an example, to map the B and T epitopes present in the complete HBHA molecule, hydrophobicity profiles are used (19). Computer prediction of antigenic B cell determinants is also used (20).

The polypeptide selected is adsorbed onto a microtitration type plate, canula, microbead or the like. The polypeptide is bound using techniques which are known to he skilled person. Preferably, the support is a microtitration plate. The polypeptide is then diluted in a basic carbonate buffer and placed in the wells. After incubating for several hours at room temperature, a number of washes using a physiological buffer are carried out.

The polypeptide bound to the support is then incubated with a biological fluid sample. Several types of biological fluids can be used, obtained from animals or humans. More particularly, the biological fluid can be obtained from serum, lymph, saliva or urine or it can be isolated from tissues such as cells of the lung. Incubation is carried out using the normal procedures. Here, the sera from patients are diluted and brought into contact with the peptide sequence bound to the plate. Incubation of about one hour is followed by several washes with a physiological buffer. The anti-HBHA antibodies bonded to the polypeptide of the invention are then revealed either with the labelled antibodies directed against the anti-HBHA antibodies, or with non labelled antibodies directed against the anti-HBHA antibodies then with labelled antibodies directed against the non labelled antibodies.

The antibodies can be labelled radioactively but in general, a further normal type of labelling is preferred. Fluorescent substances such as esithiocyanatefluoriscein or enzymes such as alkaline phosphatase, peroxidase or biotin/streptavidin are routinely used labels. The choice of labelled on non labelled antibodies depends on the animal from which the biological fluids originate. If the biological fluid is human, the antibodies used are directed against human immunoglobulins.

Binding between the anti-HBHA antibodies and the labelled or non labelled antibodies is carried out using the normal techniques. As an example, the reaction takes place over one hour at room temperature and after several washes, a labelling substrate is added.

The invention also provides a kit for detecting the presence of anti-HBHA antibodies in a sample of a biological fluid. The kit comprises a polypeptide, or one or more imunogenic regions of the HBHA, adsorbed on a support and optionally, a labelled antibody (and if necessary a non labelled antibody) as well as the normal buffers and a substrate for the label.

SEQUENCE LISTING

```
<160> NUMBER OF SEQ ID NOS: 20

<210> SEQ ID NO 1
<211> LENGTH: 39
<212> TYPE: PRT
<213> ORGANISM: Mycobacterium
<220> FEATURE:
<223> OTHER INFORMATION: sequence comprising a region involved in
      interactions with sulphated glycoconjugates and in
      heparin binding

<400> SEQUENCE: 1

Lys Lys Ala Ala Pro Ala Lys Lys Ala Ala Pro Ala Lys Lys Ala Ala
  1               5                  10                  15

Pro Ala Lys Lys Ala Ala Ala Lys Lys Ala Pro Ala Lys Lys Ala Ala
              20                  25                  30

Ala Lys Lys Val Thr Gln Lys
          35
```

```
<210> SEQ ID NO 2
<211> LENGTH: 10
<212> TYPE: PRT
<213> ORGANISM: Mycobacterium
<220> FEATURE:
<223> OTHER INFORMATION: peptide S1441

<400> SEQUENCE: 2

Lys Ala Glu Gly Tyr Leu Glu Ala Ala Thr
 1               5                  10

<210> SEQ ID NO 3
<211> LENGTH: 18
<212> TYPE: PRT
<213> ORGANISM: Mycobacterium
<220> FEATURE:
<221> NAME/KEY: CDS
<222> LOCATION: (1)
<223> OTHER INFORMATION: peptide S1443; Xaa can be any amino acid

<400> SEQUENCE: 3

Xaa Glu Gly Tyr Val Asp Gln Ala Val Glu Leu Thr Gln Glu Ala Leu
 1               5                  10                  15

Gly Lys

<210> SEQ ID NO 4
<211> LENGTH: 9
<212> TYPE: PRT
<213> ORGANISM: Mycobacterium
<220> FEATURE:
<221> NAME/KEY: CDS
<222> LOCATION: (1), (4) and (8)
<223> OTHER INFORMATION: peptide S1446; Xaa can be any amino acid

<400> SEQUENCE: 4

Xaa Gln Glu Xaa Leu Pro Glu Xaa Leu
 1               5

<210> SEQ ID NO 5
<211> LENGTH: 7
<212> TYPE: PRT
<213> ORGANISM: Mycobacterium
<220> FEATURE:
<223> OTHER INFORMATION: Peptide S1447

<400> SEQUENCE: 5

Phe Thr Ala Glu Glu Leu Arg
 1               5

<210> SEQ ID NO 6
<211> LENGTH: 17
<212> TYPE: DNA
<213> ORGANISM: Mycobacterium
<220> FEATURE:
<223> OTHER INFORMATION: Oligonucleotide originated from the S1441
      peptide (oligo S1441)

<400> SEQUENCE: 6
aaggcsgagg gstacct                                                17

<210> SEQ ID NO 7
<211> LENGTH: 17
<212> TYPE: DNA
<213> ORGANISM: Mycobacterium
<220> FEATURE:
<223> OTHER INFORMATION: Oligonucleotide originated from the S1441
      peptide (reverse oligo S1441)
```

```
<400> SEQUENCE: 7
aggtasccct csgcctt                                                    17

<210> SEQ ID NO 8
<211> LENGTH: 17
<212> TYPE: DNA
<213> ORGANISM: Mycobacterium
<220> FEATURE:
<223> OTHER INFORMATION: Oligonucleotide originated from the S1443
      peptide (oligo S1443)

<400> SEQUENCE: 8
gaccaggcsg tsgagct                                                    17

<210> SEQ ID NO 9
<211> LENGTH: 17
<212> TYPE: DNA
<213> ORGANISM: Mycobacterium
<220> FEATURE:
<223> OTHER INFORMATION: Oligonucleotide originated from the S1443
      peptide (reverse oligo S1443)

<400> SEQUENCE: 9
agctcsacsg cctggtc                                                    17

<210> SEQ ID NO 10
<211> LENGTH: 21
<212> TYPE: DNA
<213> ORGANISM: Mycobacterium
<220> FEATURE:
<223> OTHER INFORMATION: Oligonucleotide named HBHASeq1 and used for
      sequencing the gene coding for HBHA

<400> SEQUENCE: 10
agccggtaca acgagctggt c                                               21

<210> SEQ ID NO 11
<211> LENGTH: 21
<212> TYPE: DNA
<213> ORGANISM: Mycobacterium
<220> FEATURE:
<223> OTHER INFORMATION: Oligonucleotide named  HBHA Seq1inv and  used
      for sequencing the gene coding for HBHA

<400> SEQUENCE: 11
gaccagctcg ttgtaccggc t                                               21

<210> SEQ ID NO 12
<211> LENGTH: 19
<212> TYPE: DNA
<213> ORGANISM: Mycobacterium
<220> FEATURE:
<223> OTHER INFORMATION: Oligonucleotide named HBHASeq2 and  used
      for sequencing the gene coding for HBHA

<400> SEQUENCE: 12
catccaacac gtcgactcc                                                  19

<210> SEQ ID NO 13
<211> LENGTH: 19
<212> TYPE: DNA
<213> ORGANISM: Mycobacterium
<220> FEATURE:
<223> OTHER INFORMATION: Oligonucleotide named HBHA Seq3 and used for
      sequencing the gene coding for HBHA
```

```
<400> SEQUENCE: 13
ttgatgtcat caatgttcg                                                    19

<210> SEQ ID NO 14
<211> LENGTH: 19
<212> TYPE: DNA
<213> ORGANISM: Mycobacterium
<220> FEATURE:
<223> OTHER INFORMATION: Oligonucleotide named HBHA Seq4 and used for
      sequencing the gene coding for HBHA

<400> SEQUENCE: 14
cgtggaccag gcggtggag                                                    19

<210> SEQ ID NO 15
<211> LENGTH: 21
<212> TYPE: DNA
<213> ORGANISM: Mycobacterium
<220> FEATURE:
<223> OTHER INFORMATION: Oligonucleotide named HBHA Seq 5 and used for
      sequencing the gene coding for HBHA

<400> SEQUENCE: 15
gacgatcagg aggtttcccc g                                                 21

<210> SEQ ID NO 16
<211> LENGTH: 24
<212> TYPE: DNA
<213> ORGANISM: Mycobacterium
<220> FEATURE:
<223> OTHER INFORMATION: Oligonucleotide named reverse primer and used
      for sequencing the gene coding for HBHA

<400> SEQUENCE: 16
agcggataac aatttcacac agga                                              24

<210> SEQ ID NO 17
<211> LENGTH: 149
<212> TYPE: DNA
<213> ORGANISM: Mycobacterium
<220> FEATURE:
<223> OTHER INFORMATION: nucleotide sequence and amino sequence  of a
      fragment of HBHA deduced from a PCR fragment of chromosomal BCG
      DNA
<221> NAME/KEY: CDS
<222> LOCATION: (1)..(147)

<400> SEQUENCE: 17 aag gcc gag ggc tac ctc gag gcc gcg act agc cgg tac aac gag ctg        48
Lys Ala Glu Gly Tyr Leu Glu Ala Ala Thr Ser Arg Tyr Asn Glu Leu
 1               5                  10                  15 gtc gag cgc ggt gag gcc gct cta gag cgg ctg cgc agc cag cag agc        96
Val Glu Arg Gly Glu Ala Ala Leu Glu Arg Leu Arg Ser Gln Gln Ser
             20                  25                  30 ttc gag gaa gtg tcg gcg ccc gcc gaa ggc tac gtg gac cag gcg gtc       144
Phe Glu Glu Val Ser Ala Pro Ala Glu Gly Tyr Val Asp Gln Ala Val
         35                  40                  45 gag ct                                                                 149
Glu

<210> SEQ ID NO 18
<211> LENGTH: 49
<212> TYPE: PRT
<213> ORGANISM: Mycobacterium
<223> OTHER INFORMATION: amino sequence of a fragment of HBHA deduced
      from a PCR fragment of chomosomal BCG DNA
```

<400> SEQUENCE: 18

Lys Ala Glu Gly Tyr Leu Glu Ala Ala Thr Ser Arg Tyr Asn Glu Leu
 1               5                  10                  15

Val Glu Arg Gly Glu Ala Ala Leu Glu Arg Leu Arg Ser Gln Gln Ser
            20                  25                  30

Phe Glu Glu Val Ser Ala Pro Ala Glu Gly Tyr Val Asp Gln Ala Val
        35                  40                  45

Glu

<210> SEQ ID NO 19
<211> LENGTH: 1097
<212> TYPE: DNA
<213> ORGANISM: Artificial Sequence
<220> FEATURE:
<223> OTHER INFORMATION: Description of Artificial Sequence: DNA
      sequence of the BCG gene coding for HBHA
<221> NAME/KEY: CDS
<222> LOCATION: (331)..(924)
<223> OTHER INFORMATION: CDS from 811 to 828, from 829 to 846, from 847
      to 864, from 865 to 885 and from 895 to 915 : peptide which may be
      particularly involved in interactions with sulphated
      glycoconjugates

<400> SEQUENCE: 19

| | |
|---|---:|
| cggctggcgg gtaatcaaac ctgaaggaca gtcatctggg tgaggtcgac cgcaggctga | 60 |
| tccagccgat cggccggcgc tgccaacag cgactccgtc gatgacgtgc agcaaaggag | 120 |
| acatgtagtg accggatcag ctgggcctga catctacgaa ctcgaccgac aaccgacccg | 180 |
| acgatcagga ggtttccccg gcaagtcgcg tgccatgtca atccgcgggt cttgactagt | 240 |
| cctccctgga ggagccgacg cttgccccaa cgtccagacc aaagatgtaa gaacgccgat | 300 |

```
atcagaaaat agttaatgaa aggaatacccc atg gct gaa aac tcg aac att gat        354
                                    Met Ala Glu Asn Ser Asn Ile Asp
                                     1               5 gac atc aag gct ccg ttg ctt gcc gcg ctt gga gcg gcc gac ctg gcc        402
Asp Ile Lys Ala Pro Leu Leu Ala Ala Leu Gly Ala Ala Asp Leu Ala
     10                  15                  20 ttg gcc act gtc aac gag ttg atc acg aac ctg cgt gag cgt gcg gag        450
Leu Ala Thr Val Asn Glu Leu Ile Thr Asn Leu Arg Glu Arg Ala Glu
 25                  30                  35                  40 gag act cgt acg gac acc cgc agc cgg gtc gag gag agc cgt gct cgc        498
Glu Thr Arg Thr Asp Thr Arg Ser Arg Val Glu Glu Ser Arg Ala Arg
             45                  50                  55 ctg acc aag ctg cag gaa gat ctg ccc gag cag ctc acc gag ctg cgt        546
Leu Thr Lys Leu Gln Glu Asp Leu Pro Glu Gln Leu Thr Glu Leu Arg
         60                  65                  70 gag aag ttc acc gcc gag gag ctg cgt aag gcc gcc gag ggc tac ctc        594
Glu Lys Phe Thr Ala Glu Glu Leu Arg Lys Ala Ala Glu Gly Tyr Leu
 75                  80                  85 gag gcc gcg act agc cgg tac aac gag ctg gtc gag cgc ggt gag gcc        642
Glu Ala Ala Thr Ser Arg Tyr Asn Glu Leu Val Glu Arg Gly Glu Ala
         90                  95                 100 gct cta gag cgg ctg cgc agc cag cag agc ttc gag gaa gtg tcg gcg        690
Ala Leu Glu Arg Leu Arg Ser Gln Gln Ser Phe Glu Glu Val Ser Ala
105                 110                 115                 120 ccc gcc gaa ggc tac gtg gac cag gcg gtg gag ttg acc cag gag gcg        738
Pro Ala Glu Gly Tyr Val Asp Gln Ala Val Glu Leu Thr Gln Glu Ala
             125                 130                 135 ttg ggt acg gtc gca tcg cag acc cgc gcg gtc ggt gag cgt gcc gcc        786
Leu Gly Thr Val Ala Ser Gln Thr Arg Ala Val Gly Glu Arg Ala Ala
```

-continued

```
                140                 145                 150
aag ctg gtc ggc atc gag ctg cct aag aag gct gct ccg gcc aag aag      834
Lys Leu Val Gly Ile Glu Leu Pro Lys Lys Ala Ala Pro Ala Lys Lys
        155                 160                 165 gcc gct ccg gcc aag aag gcc gct ccg gcc aag aag gcg gcg gcc aag      882
Ala Ala Pro Ala Lys Lys Ala Ala Pro Ala Lys Lys Ala Ala Ala Lys
        170                 175                 180 aag gcg ccc gcg aag aag gcg gcg gcc aag aag gtc acc cag aag          927
Lys Ala Pro Ala Lys Lys Ala Ala Ala Lys Lys Val Thr Gln Lys
185                 190                 195 tagtcgggct ccgaatcacc atcgactccg agtcgcccac ggggcgactc ggagtcgacg     987
tgttggatgc aaaccgcata gtctgaatgc gtgagccacc tcgtgggtac cgtcatgctg    1047
gtattgctgg tcgccgtctt ggtgacagcg gtgtacgcgt tgtgcatgc                1097
```

<210> SEQ ID NO 20
<211> LENGTH: 199
<212> TYPE: PRT
<213> ORGANISM: Mycobacterium
<223> OTHER INFORMATION: Amino acid for HBHA

<400> SEQUENCE: 20

```
Met Ala Glu Asn Ser Asn Ile Asp Asp Ile Lys Ala Pro Leu Leu Ala
 1               5                  10                  15

Ala Leu Gly Ala Ala Asp Leu Ala Leu Ala Thr Val Asn Glu Leu Ile
                20                  25                  30

Thr Asn Leu Arg Glu Arg Ala Glu Glu Thr Arg Thr Asp Thr Arg Ser
        35                  40                  45

Arg Val Glu Glu Ser Arg Ala Arg Leu Thr Lys Leu Gln Glu Asp Leu
    50                  55                  60

Pro Glu Gln Leu Thr Glu Leu Arg Glu Lys Phe Thr Ala Glu Glu Leu
65                  70                  75                  80

Arg Lys Ala Ala Glu Gly Tyr Leu Glu Ala Ala Thr Ser Arg Tyr Asn
                85                  90                  95

Glu Leu Val Glu Arg Gly Glu Ala Ala Leu Glu Arg Leu Arg Ser Gln
            100                 105                 110

Gln Ser Phe Glu Glu Val Ser Ala Pro Ala Glu Gly Tyr Val Asp Gln
        115                 120                 125

Ala Val Glu Leu Thr Gln Glu Ala Leu Gly Thr Val Ala Ser Gln Thr
    130                 135                 140

Arg Ala Val Gly Glu Arg Ala Ala Lys Leu Val Gly Ile Glu Leu Pro
145                 150                 155                 160

Lys Lys Ala Ala Pro Ala Lys Lys Ala Ala Pro Ala Lys Lys Ala Ala
                165                 170                 175

Pro Ala Lys Lys Ala Ala Lys Lys Ala Pro Ala Lys Lys Ala Ala
            180                 185                 190

Ala Lys Lys Val Thr Gln Lys
            195
```

BIBLIOGRAPHY

1. Smith, P. G., & Moss, A. R. (1994) in *Tuberculosis, Pathogenesis, Protection, and Control*, ed. Bloom, B. R. (ASM Press, Washington, D.C.), pp. 47–59.
2. Raviglione, M. C., Snider, D. E., & Kochi, A. (1995) *J. Am. Med. Assoc.* 273, 220–226.
3. Noordeen, S. K., Bravo, L. L., & Sundaresan, T. K. (1992) *Bull. WHO* 70, 7.
4. Horsburgh, C. R. (1991) *N. Engl. J. Med.* 324, 1332.
5. Barnes, P. F., Bloch, A. B., Davidson, P. T., & Snider, D. E. (1991) *N. Engl. J. Med.* 324, 1644.
6. Bloch, A. B., Cauthen, G. M., Onorato, I. M., Dansbury, K. G., Kelly, G. D., Driver, C. R., & Snider, D. E. (1994) *J. Am. Med. Assoc.* 271, 665–671.
7. Bloom, B. R., & Murray, C. L. (1992) *Science* 257, 1005–1064.
8. Riley, L. W. (1995) *Trends Microbiol.* 3, 27–31.

9. Shepard, C. C. (1957) *J. Exp. Med.* 105, 39–48.
10. Schlesinger, L. S., Bellinger-Kawahara, C. G., Payne, N. R., & Horwitz, M. A. (1990) J. Immunol. 144, 2771–2750.
11. Schlesinger, L. S., & Horwitz, M. A. (1990) *J. Clin. Invest.* 85, 1304–1314.
12. Hirsch, C. S., Ellner, J. J., Russell, D. G., & Rich, E. A. (1994) *J. Immunol.* 152, 743–753.
13. Laernmli, U. K. (1970) *Nature* (London) 227, 680–685.
14. Rouse, D. A., Morris, S. L., Karpus, A. B., Mackall, J. C., Probst, P. G., & Chaparas, S. D. (1991) *Infect. Immun.* 59, 2595–2600.
15. Wiker, H. G., & Harboe, M. (1992) *Microbiol Rev.* 56, 648–661.
16. Kremer, L., Baulard, A., Estaquier, J., Poulain-Godefroy, O., & Locht, C. (1995) *Mol. Microbiol* 17, 913–922.
17. Sambrook, J., Fritsch, E. F., and Maniatis, T. (1989) *Molecular Cloning. A Laboratory Manual.* Cold Spring Harbor, N.Y.: Cold Spring Harbor Laboratory Press.
18. A. D. CARDIN & WEINTRAUB, 1989, Molecular modelling of protein glycoaminoglycans interactions, Arteriosclerosis, 9, 21–32.
19. T. P. Hopp, 1989, Use of hydrophilicity plotting procedures to identify protein antigenic segments and other interaction sites, Methods in Enzymology, 178, 571–585.
20. V. Krchnak, O. Mach and A. Maly, 1989, Computer prediction of B-cell determinants from protein amino acid sequences based on incidence of β turns, Methods in Enzymology, 178, 586–611.

What is claimed is:

1. A kit for serological diagnosis of mycobacterial infections comprising at least:
   a) a reactant consisting of:
      (i) an HBHA protein purified from a preparation of mycobacterium cell walls, or a fragment thereof, determined by epitope mapping; or
      (ii) a fragment comprised in the last 30 to 50 amino acids in a C-terminal portion of said HBHA protein or in the last 50 C-terminal amino acids of SEQ ID NO. 19; or
      (iii) a recombinant peptide sequence which is obtainable by expression in a host cell of a polynucleotide sequence of SEQ ID NO. 19, and wherein said recombinant peptide sequence is an HBHA mycobacterial antigen enabling the adhesion of mycobacteria to the sulphated glucides of epithelial cells;
      said reactant being coupled to or adsorbed on a support;
   b) an anti-antibody antibody, modified such that a detection signal can be coupled thereto.

2. The kit according to claim 1, wherein said anti-antibody antibody is specific for human immunoglobulins.

3. The kit according to claim 1, wherein said anti-antibody antibody is directly or indirectly labelled, either using a labelling substance, or by an enzyme which emits a labelling signal through the transformation of its substrate.

* * * * *